United States Patent [19]

Hoenig et al.

[11] Patent Number: 5,685,969

[45] Date of Patent: Nov. 11, 1997

[54] SENSOR ARRANGEMENT

[75] Inventors: Eckhardt Hoenig, Erlangen; Volker Lehmann; Ulf Buerker, both of Munich, all of Germany

[73] Assignee: Siemens Aktiengesellschaft, Munich, Germany

[21] Appl. No.: 313,884

[22] Filed: Sep. 28, 1994

[30] Foreign Application Priority Data

Sep. 28, 1993 [DE] Germany ............................. 43 33 001.0

[51] Int. Cl.⁶ ..................................................... C25D 5/02
[52] U.S. Cl. .......................... 205/123; 205/157; 205/210; 205/229; 205/333; 205/665; 205/666; 205/640; 205/674; 205/667; 422/82.01
[58] Field of Search ............................... 205/674, 665, 205/667, 666, 640, 210, 157, 123, 333, 229; 422/82.01

[56] References Cited

U.S. PATENT DOCUMENTS

| | | | |
|---|---|---|---|
| 4,275,406 | 6/1981 | Muller et al. | 357/26 |
| 4,433,470 | 2/1984 | Kameyama et al. | 29/577 C |
| 4,555,661 | 11/1985 | Benson et al. . | |
| 4,685,197 | 8/1987 | Tigelaar et al. | 437/195 |
| 4,759,822 | 7/1988 | Vetanen et al. | 156/644 |
| 4,808,259 | 2/1989 | Jillie, Jr. et al. | 156/643 |
| 4,827,323 | 5/1989 | Tigelaar et al. | 357/51 |
| 4,916,114 | 4/1990 | Hoenig | 505/1 |
| 5,262,021 | 11/1993 | Lehmann et al. | 204/129.55 |
| 5,306,647 | 4/1994 | Lehmann et al. | 437/2 |
| 5,338,416 | 8/1994 | Mlcak et al. | 204/129.3 |
| 5,365,405 | 11/1994 | Hoenlein et al. | 361/766 |
| 5,371,410 | 12/1994 | Chen et al. | 257/750 |
| 5,403,752 | 4/1995 | Brochhaus et al. | 437/3 |
| 5,464,509 | 11/1995 | Mlcak et al. | 204/129.3 |
| 5,500,385 | 3/1996 | Wendt et al. | 437/60 |

FOREIGN PATENT DOCUMENTS

| | | |
|---|---|---|
| 0317871 | 5/1989 | European Pat. Off. . |
| 3519435 | 12/1986 | Germany . |

Primary Examiner—Robert J. Warden
Assistant Examiner—Sharidan Carrillo
Attorney, Agent, or Firm—Hill, Steadman & Simpson

[57] ABSTRACT

A sensor arrangement having a substrate of doped silicon with channels in a principal face, a selective means for detecting a material, the selective means covering the principal face without filling the channels, and a measuring instrument for registering a physical quantity dependent on the influence of a material is provided. A catalytic layer is particularly used as selective means and a temperature sensor is particularly used as measuring instrument. Alternatively, the sensor arrangement is fashioned as a capacitor having a porous cooperating electrode. The channels are preferably produced by electrochemical etching.

13 Claims, 2 Drawing Sheets

SENSOR ARRANGEMENT

BACKGROUND OF THE INVENTION

1. Field of the Invention

The present invention is directed generally to semiconductor structures and more specifically to a semiconductor sensor arrangement.

2. Description of the Related Art

Catalytic reactions are suitable for the selective detection of gases or liquids. In those catalytic reactions that proceed exothermally, the material to be detected can be measured via a temperature change, for example, with a temperature-dependent resistance. In other catalytic reactions, the material to be detected is split into reaction products that are in turn detected with a sensor element.

It is known, for example, (see, DE 35 19 485 A1 or European patent application no. 88118985.6) to employ a MOS-like semiconductor structure as a gas sensor, whereby an oxide layer is arranged on a semiconductor body and an electrode is arranged on this oxide layer, and whereby an electrode is a metal. A catalytic reaction occurs at the surface of the metal electrode. The semiconductor structure can thereby be produced as a MOS transistor or as a capacitor. Reaction products are formed in the catalytic reaction that diffuse through the electrode into the oxide layer and/or to the boundary surface between the oxide and the semiconductor surface. A shift of the cutoff voltage thereby occurs given a MOS transistor and a variation of the capacitance occurs given a capacitor. The cutoff voltage or, respectively, the capacitance is then registered as a measured quantity.

For detecting hydrogen, for example, it is known to employ palladium, rhodium, platinum or nickel as catalysts. Also, silver is suitable for detecting oxygen. An electrode of palladium is suitable for detecting CO. The electrode has a multitude of holes extending down to the metal/oxide boundary layer. β-carotene is likewise suitable as catalyst.

Gas sensors are known under the name of "Pellistor" and function according to the principles of calorimetry. The gas sensor is thereby composed of two resistance wires. A porous ceramic pellet is sintered onto each wire. A catalyst is applied onto one of the two ceramic pellets, and the material to be detected reacts exothermally at the surface of the catalyst. Due to the temperature change, a change in resistance relative to the second resistance wire occurs for the resistance wire having the ceramic pellet coated with catalyst. This change in resistance is measured via a bridge circuit.

Calorimetric effects in conjunction with catalysts are known from the literature. Hydrogen burns exothermally in a platinum catalyst. NO is formed from $NH_3$ at a catalyst of platinum or platinum-rhodium given temperatures between 200° and 250° C. $NO_2$ is formed from NO at a catalyst of $Al_2O_3$—$SiO_2$ gel at temperatures around 100° C. These reactions occur in an oxygen atmosphere. $SO_2$ reacts with oxygen to form $SO_3$ at elevated temperature at the surface of a catalyst of platinum, $Fe_2O_3$ or $V_2O_5$. CO can be oxidized into $CO_2$ above 150° C. with the assistance of a catalyst of palladium. At temperatures between 200° and 400° C., methanol reacts with oxygen at a silver catalyst to form HCHO.

Zelites that are also referred to as molecular sieves also act selectively. These have the property of allowing molecules with a specific size and smaller to pass, whereas larger molecules are prevented from passing. It is known to provide layers of zelite on sensor arrangements as a selective means in order to select molecules having a predetermined maximum size.

The effect caused by the material to be detected is often relatively small, so that measurable signals can only be achieved given a certain area size of the selective means. Since the known sensor arrangements are planar, this often involves a structural size of the sensor arrangement that is disturbing for many applications.

SUMMARY OF THE INVENTION

It is an object of the present invention to provide a sensor arrangement having improved sensitivity per unit of area relative to known sensor arrangements.

Another object of the present invention is to provide a manufacturing method for producing such a sensor arrangement.

The objects of the present invention are inventively achieved in a sensor arrangement having a substrate of doped silicon having a first principal face with channels therein, selective means for detecting a material by interacting therewith, the selective means covering the first principal face without filling the channels; and measuring means for registering a physical quantity dependent on the interaction of the material to be detected with said selective means.

The object of providing a manufacturing method for producing such a sensor arrangement is achieved in a method for manufacturing a sensor arrangement having the steps of providing a substrate of n-doped silicon, having a first principal face; forming channels in the first principal face by an electrochemical etching in a fluoride-containing, acidic electrolyte, wherein the first principal face is in contact with the electrolyte and a voltage is applied between the electrolyte and the substrate, the substrate being connected as anode, to set a current density influencing the etching erosion; and depositing a selective means as a layer on the entire surface of the channels.

The sensor arrangement of the invention a substrate of doped silicon that has channels in a first principal surface. The first principal surface is covered with a selective means for the detection of a material; this selective means does not fill the channels. The effective area of the selective means is enlarged by a multiple in this way compared to the geometrical area of the sensor arrangement. An enhanced sensitivity per geometrical unit of area of the sensor arrangement is achieved with the increase in the size of the effective area.

The channels in the first principal face of the substrate are preferably produced by electrochemical etching. To that end, a substrate of n-doped silicon is used whose first principal face is brought into contact with a fluoride-containing, acidic electrolyte. A voltage is applied between the electrolyte and the substrate, so that the substrate is connected as anode. The voltage is set such that a current density that influences the etching erosion is established.

Since the substrate is connected as anode in the electrochemical etching, minority charge carriers move in the n-doped silicon to the first principal face in contact with the electrolyte. A space charge zone is formed thereat. Since the field strength is greater in the region of depressions in the first principal face than beyond these depressions, the minority charge carriers preferably move to these points. A structuring of the surface thereby occurs. More minority charge carriers move to these points because the increased field strength and the etching attack at this location is greater, the deeper an initially small irregularity becomes due to the etching. The channels grow into the depth of the substrate in this way.

Channels having hole diameters between 20 µm and 50 nm and hole depths up to 500 µm can be produced well in this way. Increases in surface area by a factor 25–2500 can be achieved as a result thereof.

According to one embodiment of the invention, the selective means has a catalytic layer at whose surface the material to be detected reacts exothermally. A temperature sensor that is sensitive to temperature changes of the substrate is provided as a measuring instrument in this case. The surface of the catalytic layer highly enlarged by the channels effects temperature changes of the substrate in the measurable range. In particular, the temperature sensor is arranged as a temperature-sensitive resistor on a second principal face that lies opposite the first principal face. The catalytic layer particularly contains palladium, rhodium, platinum or silver.

According to a further embodiment, the sensor arrangement is produced as a capacitor. To that end, a dielectric layer that does not fill the channels is arranged on the first principal face. Also, a conductive layer that does not fill the channels is arranged on the surface of the dielectric layer. The conductive layer enables a selected diffusion into the dielectric layer that is characteristic of the material to be detected. In this case, the dielectric layer and the conductive layer form the selective means. The entire capacitor acts as a measuring instrument.

In this embodiment, the conductive layer is transmissive, for example, only for the material to be detected. This, for example, is the case when the conductive layer is amorphous or polycrystalline doped silicon and when the material to be detected is hydrogen.

Alternatively, the conductive layer has a catalytic layer at whose surface the material to be detected is split into fragments that diffuse through the conductive layer into the dielectric layer. For example, palladium is suitable as the catalytic layer in this case.

It is likewise possible to provide reactive chemical material or radiating radioactive material in the conductive layer. This material reacts with the material to be detected upon formation of reaction products that in turn diffuse into the dielectric layer.

When the sensor arrangement is produced as a capacitor, then the change in capacitance of the capacitor is registered as a measured signal. This is advantageously documented in a resonant circuit arrangement via the frequency change thereof. It lies within the scope of the invention to provide a thin-film coil on the substrate. The thin-film coil forms a resonant circuit with the capacitor formed of substrate, dielectric layer and conductive layer. The frequency change of this resonant circuit is measurable as a sensor signal. The sensor signal is preferably measured in a contactless manner by inductive coupling.

The channels in the sensor arrangement of the invention can be both continuous as well as open at one side. The material to be detected is conducted through the channels in flow-through given continuous channels. A high response time of the sensor arrangement is thereby achieved.

The material proceeds by drive-in into channels open at one side. In applications wherein it is a matter of selectivity and sensor arrangement, it is advantageous to close the channels with a protective layer that is permeable for the material to be detected. Selectively disturbing foreign bodies and foreign materials are kept away from the sensor arrangement in this way.

The sensor arrangement can be used as a chemical dosimeter by occupying or filling the channels with reactive chemical material or with radiating radioactive material that leads to specific reactions with the material to be detected and releases reaction products that diffuse through the conductive layer into the dielectric layer. The reactive temperature increase in the channels can be additionally used in this case as a selection mechanism.

The sensor arrangement is suitable for the detection of gaseous as well as liquid material. In particular, the sensor arrangement is suitable for the detection of neutral particles in plasmas, since the channel structure acts with plasma repulsion. A sensor arrangement having through channels and capacitor contacts at that side facing away from the plasma is preferably used for this application.

It lies within the scope of the invention to realize the first stages of a read-out electronics on the same substrate.

The invention shall be set forth in greater detail below with reference to the figures and to the exemplary embodiments.

DETAILED DESCRIPTION OF THE PREFERRED EMBODIMENT

Figure 1:
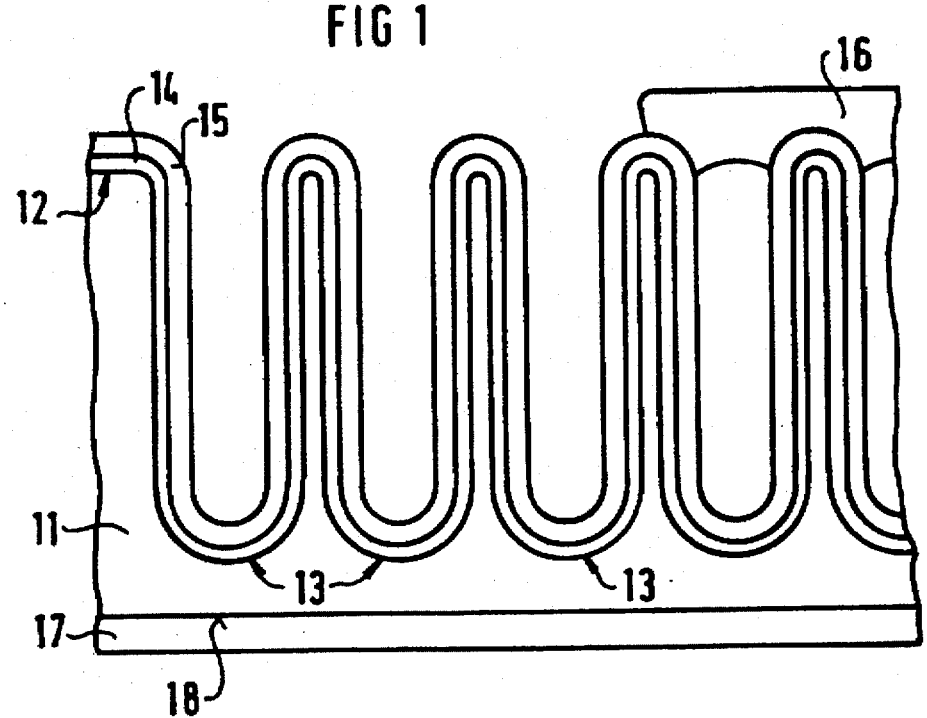
FIG. 1 shows a sensor arrangement that is produced as capacitor of the present invention.

A substrate 11 of n-doped single-crystal silicon having an electrical conductivity of, for example, 5 ohm/cm has channels 13 in a first principal face 12 (see FIG. 1). The channels 13 have an essentially round cross section with a diameter of, for example, 2 µm. The depth of the channels 13 is, for example, 50 µm. Neighboring channels 13 are separated by webs that have a width of 2 µm.

The channels 13 are produced in the substrate 11 by electrochemical etching. To that end, the first principal face 12 of the substrate 11 is brought into contact with a fluoride-containing, acidic electrolyte. The electrolyte has a hydrofluoric acid concentration by weight of 1–50%, preferably 5%. An oxidation agent, for example, hydrogen peroxide can be added to the electrolyte in order to suppress the formation of hydrogen bubbles on the first principal face 12 of the substrate 11.

The substrate 11 is connected as anode. A voltage from 0–20 volts, preferably 3 volts, is applied between the substrate 11 and the electrolyte. The substrate 11 is illuminated with light proceeding from the back side, so that a current density of, for example, 10 mA/cm$^2$ is established. Proceeding from irregularities in the first principal face 12, the channels 13 that proceed perpendicularly relative to the first principal face 12 are produced in the electrochemical etching. After an etching time of approximately 70 minutes, a depth of, for example, 50 µm is achieved for the channels 13.

The distribution of the channels 13 over the first principal face 12 can be influenced by providing the first principal face 12 with a surface topology before the electrochemical etching. To that end, depressions are produced, for example by using a photo-resist mask and subsequent alkaline etching, that correspond to the desired arrangement of the channels 13. These depressions serve as nuclei in the electrochemical etching. The electrochemical etching begins forming the channels 13 at the depressions.

A dielectric layer 14 that completely covers the first principal face 12 is arranged on the first principal face 12. The dielectric layer is thinner than half the cross section of the channels 13, so that the channels 13 are not filled by the dielectric layer 14. For example, the dielectric layer 14 is $SiO_2$. In applications where a low hole density of the dielectric layer 14 is a matter of concern, the dielectric layer 14 is preferably formed as a combination layer of $SiO_2$, $Si_3N_4$ and $SiO_2$ (ONO).

The dielectric layer 14 is covered with a conductive layer 15. At least at its surface, the conductive layer 15 is: a) a material that allows the material to be detected to selectively pass through; b) a material that reacts with the material to be detected upon formation of reaction products that can selectively diffuse into the conductive layer; or c) a material that reacts selectively with the material to be detected. For detecting hydrogen, the conductive layer 15 is formed, for example, of amorphous doped silicon, doped polycrystalline silicon or palladium. The conductive layer 15 is applied with such a thickness that the channels 13 are not filled by the conductive layer 15. What is thereby assured is that the effective surface of the conductive layer 15 at which the detection of the material occurs is larger than the base area of the sensor arrangement.

The substrate 11, the dielectric layer 14 and the conductive layer 15 form a capacitor. In the detection of the material, a diffusion of the material or, respectively, of reaction products characteristic thereof through the conductive layer 15 occurs into the dielectric layer 14. As a result thereof, the dielectric constant of the dielectric layer 14 changes, which leads to a change in the capacitance of the capacitor. For measuring the change in capacitance, the conductive layer 15 is provided with a first electrode 16, and the substrate 11 is provided with a second electrode 17. The first electrode 16 and the second electrode 17 are formed, for example, of aluminum. The first electrode 16, for example, is arranged on the first principal face 12. It is dimensioned as small as possible so that the effective area of the sensor arrangement is not unnecessarily reduced. The second electrode 17, for example, is arranged at a second principal face 18 that lies opposite the first principal face 12.

Figure 2:
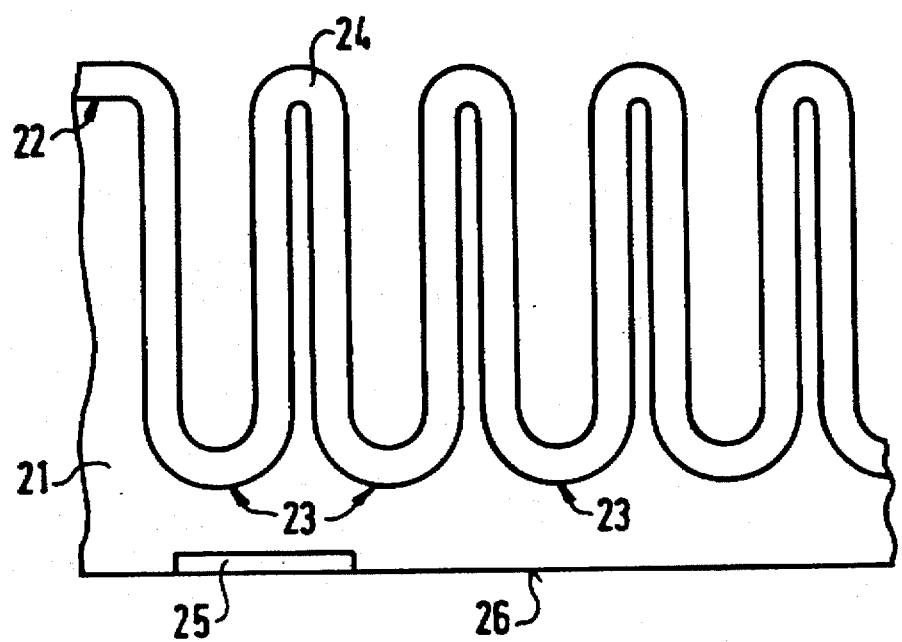
FIG. 2 shows a sensor arrangement that functions according to the calorimeter principle of the present invention.

According to a further embodiment of the invention illustrated in FIG. 2, a substrate 21 of n-doped, single-crystal silicon is provided with channels 23 in a first principal face 22. The channels 23 are produced analogous to the exemplary embodiment shown with reference to FIG. 1. The channels 23 have a diameter of, for example, 2 µm and a depth of, for example, 50 µm.

The first principal face 22 is provided with a catalytic layer 24. The catalytic layer 24 has a thickness that is less than half the cross section of the channels 22, for example, less than 1 µm. When a greater layer thickness is required for the reaction, the diameters of the channels must be correspondingly modified. The catalytic layer 24 is formed of a material at whose surface the material to be detected reacts exothermally. Due to the exothermal reaction, a modification of the temperature of the substrate 21 occurs.

A temperature sensor 25 that, for example, is arranged on or in a second principal face 26 lying opposite the first principal face 22 is provided for measuring this temperature change. For example, a temperature-dependent resistor is suitable as temperature sensor 25. This can be produced, in particular, in thin-film technology or as a pn-junction.

When hydrogen is to be detected, the catalytic layer 24 is, for example, platinum. Platinum or platinum-rhodium is suitable as catalytic layer for detecting $NH_3$ by producing NO. A catalytic layer of $Al_2O_3$—$SiO_2$ gel is suitable for detecting NO by forming $NO_2$. $SO_2$ can be detected by oxidation to form $SO_3$ by using the catalytic layer of platinum, $SE_2O_3$ or $V_2O_5$. CO can be detected with the catalytic layer of palladium by oxidation to form $CO_2$. When the catalytic layer 25 is silver, then it is suitable for detecting methanol based on the oxidation thereof to form HCHO.

Since many of these catalytic reactions occur at elevated temperature, it is expedient to heat the catalytic layer 24. When the catalytic layer 24 is a conductive material, this heating occurs, for example, by ohmic heating.

Figure 3:
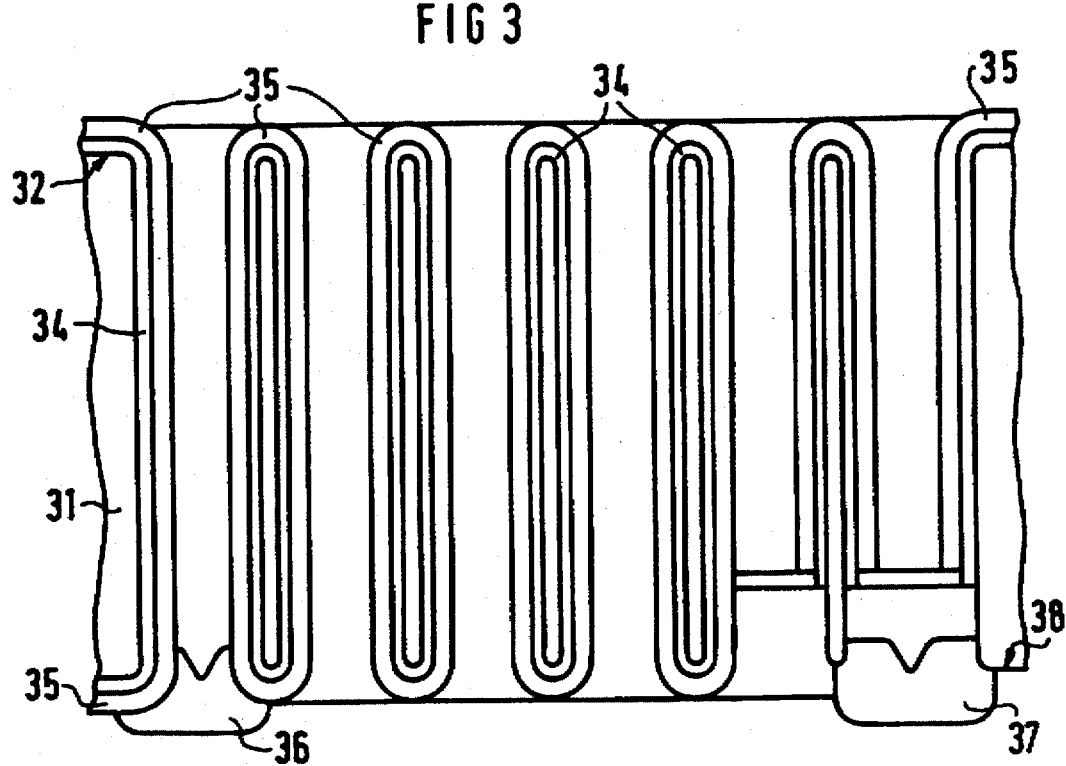
FIG. 3 shows a sensor arrangement that is produced as a capacitor and has through channels of the present invention.

According to a further embodiment of the invention illustrated in FIG. 3, a substrate 31 of n-doped, single-crystal silicon is provided with channels 33. The channels 33 traverse the entire substrate 31.

For example, the channels 33 are formed by electrochemical etching. The electrochemical etching is implemented as set forth with reference to the exemplary embodiment in FIG. 1. To that end, a first principal face 32 is brought into contact with the fluoride-containing, acidic electrolyte. The electrochemical etching is continued until the channels 33 have reached a second principal face 38 that lies opposite the first principal face 32. This is the case after approximately 600 minutes.

The entire surface of the substrate 31 is provided with a dielectric layer 34. For example, the dielectric layer 34 can be formed by thermal oxidation of $TiO_2$, anodic oxidation of $TiO_2$, or vapor phase deposition $TiO_2$, or can be vapor phase deposited layers of a layer sequence of $SiO_2$, $Si_3N_4$ and $SiO_2$. The dielectric layer 34, such as by vapor phase deposition is produced, for example, with a thickness of 20 nm.

A conductive layer 35 is applied onto the dielectric layer 34. At least at its surface, the conductive layer 35 has: a) a material that allows the material to be detected to selectively pass; b) a material that reacts with the material to be detected upon formation of reaction products that selectively diffuse through the conductive layer; or c) a material that selectively reacts with the material to be detected. For example, the conductive layer is doped amorphous silicon, doped polycrystalline silicon or palladium. The surface of the conductive layer 37 can be occupied with reactive chemical material or with emissive radioactive material.

The substrate 31, the dielectric layer 34 and the conductive layer 35 form a capacitor. For measuring the capacitance of the capacitor, the conductive layer 35 is provided with a first electrode 36 and the substrate 31 is provided with a second electrode 37. The first electrode 36 and the second electrode 37 are preferably arranged on the second principal face 38. To that end, the conductive layer 35 and the dielectric layer 34 are etched back in the region of the second electrode 37 before the production of the second electrode 37 to enable contact between the second electrode 37 and the substrate 31. The first electrode 36 and the second electrode 37 are produced, for example, of aluminum.

This embodiment of the sensor arrangement of the invention enables a flow-through measurement of the material to be detected. This embodiment is especially suited for detecting neutral particles in plasmas in plasma analysis. The plasma-repelling channel structure is thereby utilized. The sensor arrangement is aligned such that the first principal face 32 faces towards the plasma, so that the first electrode 36 and the second electrode 37 are located at the side facing away from the plasma.

Figure 4:
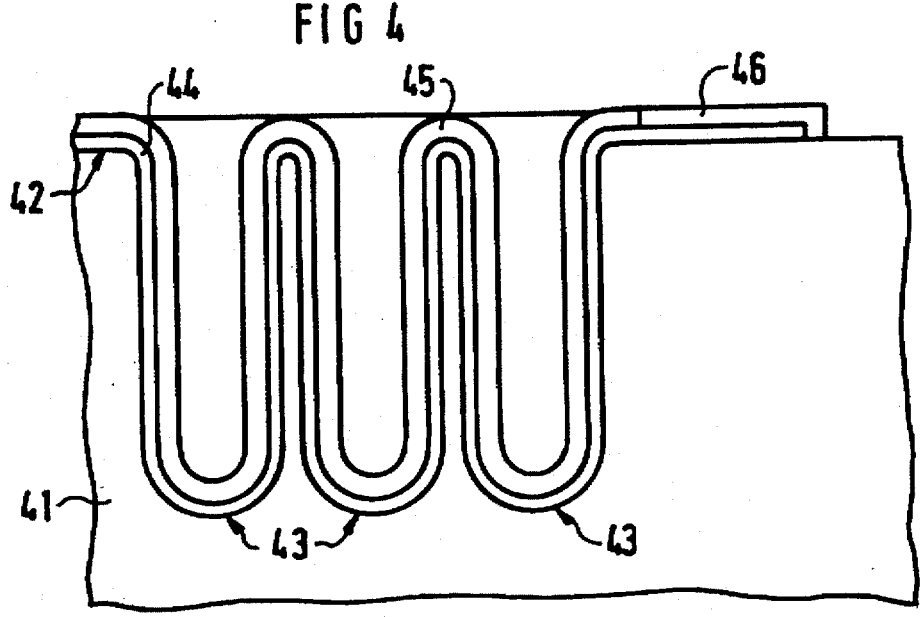
FIG. 4 shows a sensor arrangement that is produced as a capacitor and wherein a readout electronics integrated with it is provided in the substrate of the present invention.

According to a further embodiment illustrated in FIG. 4, a substrate 41 of n-doped, single-crystal silicon having a conductivity of, for example, 5 ohms/cm has a first principal face 42 provided with channel structures 43. Analogous to the exemplary embodiment set forth with reference to FIG. 1, the channel structures 43 are produced by electrochemical etching in a fluoride-containing electrolyte. The channels 43 have an essentially round cross section with a diameter of, for example, 2 μm. The channels 43 are distributed over the surface in the region of the sensor arrangement. Neighboring channels 43 are separated from one another by webs that have a width of, for example, 2 μm. The depth of the channels is, for example, 50 μm.

The surface is occupied with a dielectric layer 44 in the region of the channels 43. The dielectric layer 44 is, for example, $SiO_2$ or a triple layer of $SiO_2$, $Si_3N_4$, $SiO_2$ and has a thickness of, for example, 20 nm.

A conductive layer 45 is arranged at the surface of the dielectric layer. The conductive layer 45 is composed of a material that allows a selective drive-in of the material to be detected or a reaction product of the material to be detected into the dielectric layer 44. The conductive layer 45 is, for example, doped amorphous silicon or doped polycrystalline silicon or palladium. The conductive layer 45 can have its surface covered with catalytic material, reactive chemical material or emissive radioactive material.

The thin-film coil 46 is arranged at the surface of the substrate 41 to the side of the sensor arrangement having the channels 43. The thin-film coil 46 is insulated from the substrate 41 by an insulating layer, for example the extension of the dielectric layer 44 onto the part of the first principal face 42 wherein no channels 43 are arranged. The thin-film coil 46 is electrically connected both to the conductive layer 45 as well as to the substrate 41. The substrate 41, the dielectric layer 44 and the conductive layer 45 form a capacitor. This capacitor and the thin-film coil 46 form a resonant circuit arrangement. The capacitance of the capacitor changes due to drive-in of the material to be detected or reaction products characteristic of the material to be detected into the dielectric layer 44. This change in capacitance leads to a change in frequency of the resonant circuit arrangement. In this embodiment of the invention, the frequency change of the resonant circuit arrangement can be measured by inductive coupling while avoiding any and all contacts. This is advantageous for operating dependability and ruggedness.

The first stages of an evaluation electronics can likewise be integrated in the substrate 41 outside of the channels 43.

Although other modifications and changes may be suggested by those skilled in the art, it is the intention of the inventors to embody within the patent warranted hereon all changes and modifications as reasonably and properly come within the scope of their contribution to the art.

We claim:

1. A method for manufacturing a sensor arrangement for sensing a material, comprising the steps of:
   providing a substrate of n-doped silicon having a principal face;
   forming channels in said principal face by electrochemically etching said principal face in a fluoride-containing, acidic electrolyte in contact with said principal face while applying a voltage between said electrolyte and said substrate with said substrate connected as an anode, to set a current density influencing erosion of said principal face by said etching, said channels respectively having channel surfaces;
   depositing a catalytic layer on said channel surfaces, without filling said channels, which reacts exothermally with the material to be sensed; and
   providing a temperature sensor in temperature-sensing relationship to said catalytic layer to sense a temperature produced by the exothermal reaction of said catalytic layer and said material.

2. Method according to claim 1, wherein said step of providing a substrate of n-doped silicon is further defined by providing a <100> wafer.

3. Method according to claim 1, wherein said step of forming channels in said principal face includes illuminating a second principal face of said substrate lying opposite said principal face.

4. Method according to claim 1, wherein said step of forming channels in said principal face includes providing an electrolyte containing 1–50% by weight hydrofluoric acid as said fluoride-containing, acidic electrolyte.

5. Method according to claim 4, wherein said step of forming channels in said principal face includes providing an electrolyte additionally containing an oxidation agent as said fluoride-containing, acidic electrolyte.

6. Method according to claim 1, further comprising the step of:
   providing said principal face of said substrate with a surface topology before forming said channels, said surface topology defining an arrangement of said channels.

7. Method according to claim 1, wherein the step of depositing said catalytic layer comprises forming a dielectric layer on said channel surfaces by a process selected from a group consisting of:
   thermal oxidation of $TiO_2$, anodic oxidation of $TiO_2$, vapor phase deposition of $TiO_2$, and combined deposition of a sequence of respective layer of $SiO_2$ and $Si_3N_4$ and $SiO_2$; and
   forming of a conductive layer on said dielectric layer by vapor phase deposition.

8. A method for manufacturing a sensor arrangement for sensing a material, comprising the steps of:
   providing a substrate of n-doped silicon having a principal face;
   forming channels in said principal face by electrochemically etching said principal face in a fluoride-containing, acidic electrolyte in contact with said principal face while applying a voltage between said electrolyte and said substrate with said substrate connected as an anode, to set a current density influencing erosion of said principal face by said etching, said channels respectively having channel surfaces;
   depositing a dielectric layer on said channel surfaces by a process selected from a group consisting of thermal oxidation of $TiS_2$, anodic oxidation of $TiO_2$, vapor phase deposition of $TiO_2$, and combined deposition of a sequence of respective layers of $SiO_2$ and $Si_3N_4$ and $SiO_2$, and forming a conductive layer on said dielectric layer by vapor phase deposition, without filling said channels, said conductive layer, said dielectric layer and said substrate forming a capacitor having a capacitance which changes dependent on the material to be sensed; and
   providing a thin film coil on said substrate in series with said capacitor to form a resonant circuit having a resonant frequency which changes dependent on said changes in capacitance.

9. Method according to claim 8, wherein said step of providing a substrate of n-doped silicon is further defined by providing a <100> wafer.

10. Method according to claim 8, wherein said step of forming channels in said principal face includes illuminating a further principal face of said substrate lying opposite said principal face.

11. Method according to claim 8, wherein said step of forming channels in said principal face includes providing an electrolyte containing 1–50% by weight hydrofluoric acid as said fluoride-containing, acidic electrolyte.

12. Method according to claim 11, wherein said step of forming channels in said principal face includes providing an electrolyte additionally containing an oxidation agent as said fluoride-containing, acidic electrolyte.

13. Method according to claim 8, further comprising the step of:
 providing said principal face of said substrate with a surface topology before forming said channels, said surface topology defining an arrangement of said channels.

* * * * *